United States Patent [19]

Inada et al.

[11] Patent Number: 5,138,151
[45] Date of Patent: Aug. 11, 1992

[54] METHOD FOR DETECTING AN ABNORMAL PORTION OF A YARN PACKAGE

[75] Inventors: Kenichi Inada, Ohtsu; Tetsuji Masai, Kyoto, both of Japan

[73] Assignee: Murata Kikai Kabushiki Kaisha, Kyoto, Japan

[21] Appl. No.: 501,236

[22] Filed: Mar. 29, 1990

[30] Foreign Application Priority Data

Apr. 4, 1989 [JP] Japan ................................. 1-85497

[51] Int. Cl.⁵ .............................................. G01N 9/04
[52] U.S. Cl. .................................. 250/223 R; 356/376
[58] Field of Search ........... 250/571, 572, 562, 223 B, 250/223 R; 356/238, 429, 430, 376

[56] References Cited

U.S. PATENT DOCUMENTS

| | | | |
|---|---|---|---|
| 4,184,769 | 1/1980 | Aeppli | 356/430 |
| 4,184,770 | 1/1980 | Pinior | 356/430 |
| 4,606,645 | 8/1986 | Matthews et al. | 250/572 |
| 4,748,334 | 5/1988 | Kobayashi et al. | 250/572 |
| 4,866,289 | 9/1989 | Kawamura et al. | 356/238 |

Primary Examiner—David C. Nelms
Assistant Examiner—S. Allen
Attorney, Agent, or Firm—Spensley Horn Jubas & Lubitz

[57] ABSTRACT

A ray having an optical axis approximately parallel with a surface of a yarn layer is irradiated against a surface of a package, and a light receiving element for receiving light reflected on an abnormal yarn on the surface of the yarn layer is provided at a position at which the reflected light is maximum to detect an abnormal yarn.

11 Claims, 5 Drawing Sheets

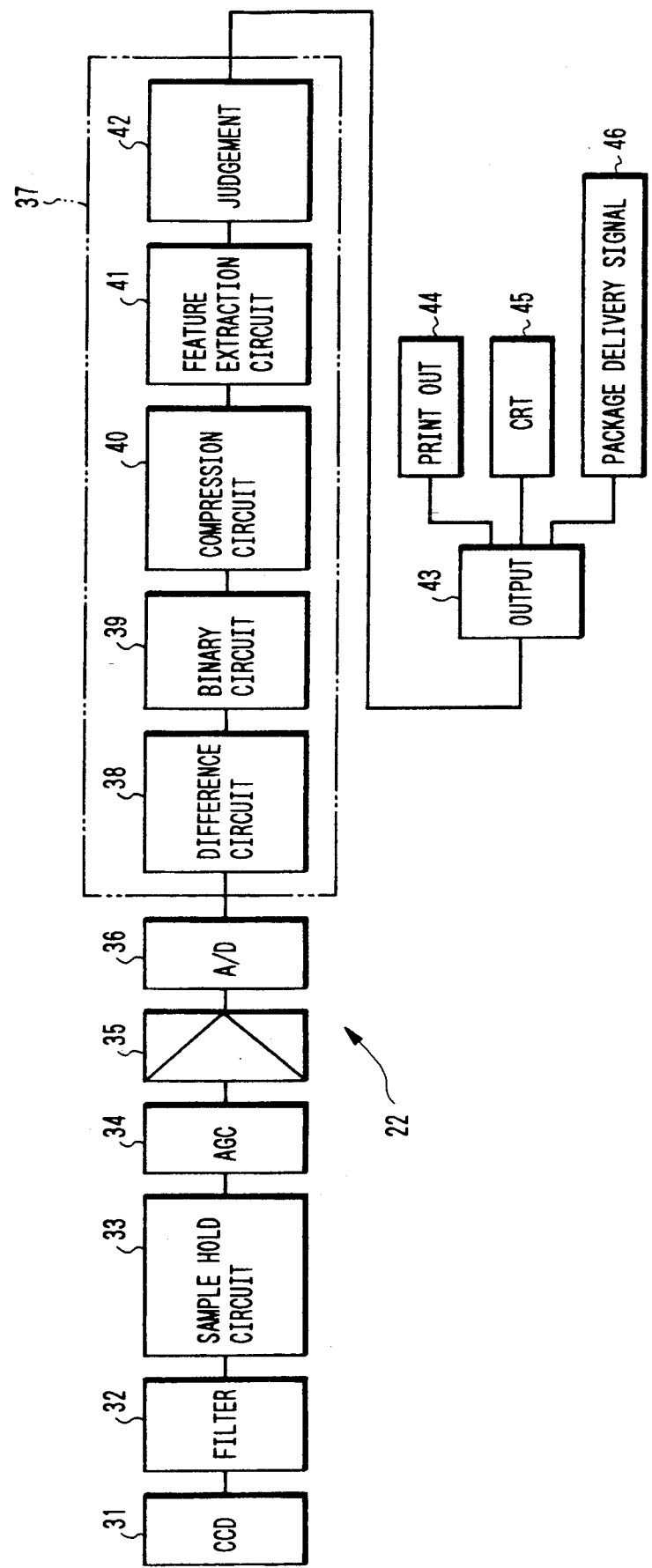

METHOD FOR DETECTING AN ABNORMAL PORTION OF A YARN PACKAGE

FIELD OF THE INVENTION

The present invention relates to a method of inspection for a wound yarn package produced by a winder, and particularly to a method of inspecting an abnormal portion such as an out-of-lease package in which a part of a yarn is in a state of cob-webbing from the end of the package.

RELATED ART STATEMENT

Recently, in spinning works, automation of the carrying and packing of a package wound by a winder has been realized. At present, only the quality inspection of a package, which is indispensable, relies upon a visual inspection.

Inspections now carried out in spinning works include (1) presence or absence of bunch wind, (2) out-of-lease, (3) mixture of kinds, (4) weight, (5) stepped wind, wrinkles, and (6) ribbon wind, which are different in various inspection contents in the works.

In the past, these inspections have been carried out on a package carrier conveyor by which a package wound by a winder is carried to an automatic packing robot. Packages visually found to be defective are ejected from the carrier conveyor, and only those accepted by inspection are carried to the automatic packing robot.

The visual inspection as described above has a limit. Therefore, various apparatus for automating the aforesaid inspections by optical means have been proposed.

The applicant has also previously proposed automatic inspection methods and apparatus as disclosed in Japanese Patent Application Laid-Open Nos. 62938/1987 and 135532/1988.

Even by the aforementioned methods, a detection error occurs particularly in detecting a single yarn out-of-lease. However, sufficient reliability has not yet been obtained.

Where an out-of-lease occurs on the side of a package of large diameter, the out-of-lease yarn is in contact with the surface of the end of a yarn layer. That is, an out-of-lease yarn on the side of a package of small diameter floats from the surface of the end of the yarn layer, in which case, a shadow caused by light appears on the surface of the yarn layer, and therefore, an out-of-lease condition could to some degree, be detected by a conventional device.

However, in the case of out-of-lease yarn on the package of a large-diameter side as described above, no shadow appears, and therefore, errors in the detection by the conventional device sometimes occur of the out-of-lease condition.

When the out-of-lease condition occurs on the side of a small diameter package, there occurs no substantial problem. However, when the out-of-lease occurs on the side of a large diameter package, yarn breakage is caused.

OBJECT AND SUMMARY OF THE INVENTION

It is an object of the present invention to solve the aforesaid problem by providing an inspection method which is effective for detection of an out-of-lease condition on the side of a large diameter cone package as well as a method which can detect an out-of-lease condition on the side of a small diameter package with a fine rugged portion on the surface of a yarn layer of a stepped wind or the like.

In the present invention, a ray having an optical axis approximately parallel with a surface of a yarn layer is irradiated against a surface of a package, and a light receiving element for receiving light reflected on an abnormal yarn on the surface of the yarn layer is provided at a position at which said reflected light is maximum to detect an abnormal yarn.

BRIEF DESCRIPTION OF THE DRAWINGS

FIG. 9 is a block diagram showing one example of a processing and analyzing device for a light signal obtained by said device;

DETAILED DESCRIPTION OF PREFERRED EMBODIMENTS

An embodiment of the present invention will be described with reference to the drawings.

Figure 1:
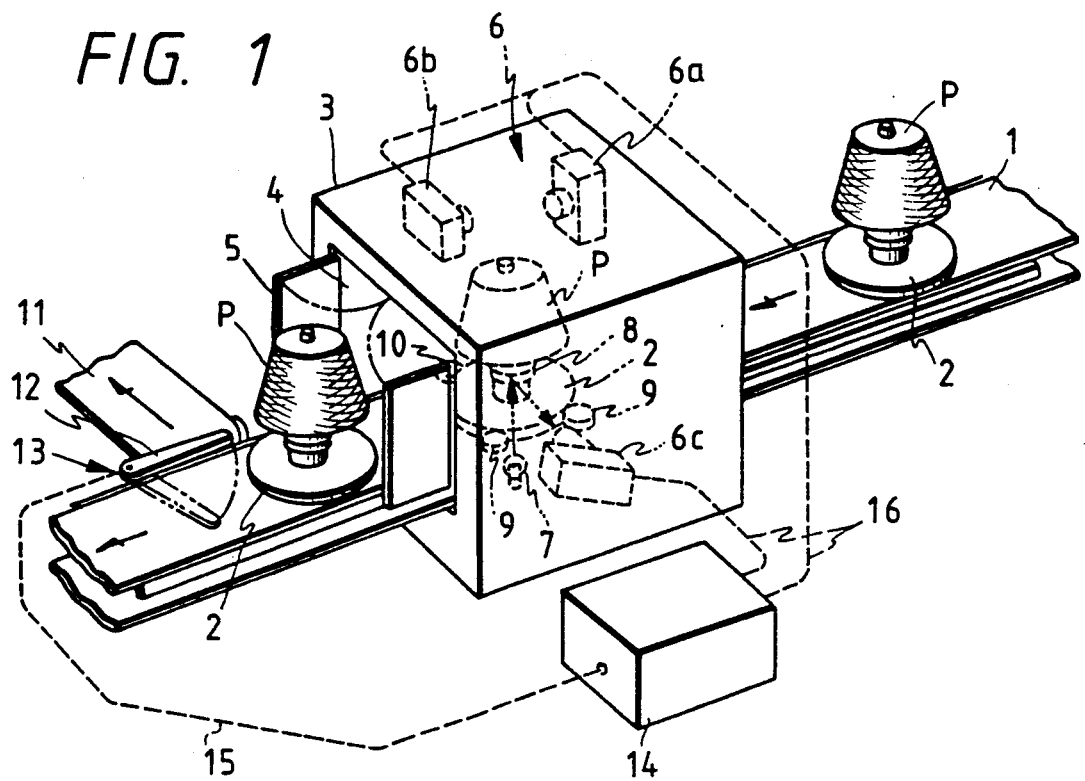
FIG. 1 is a perspective view of a schematic structure showing one example of a package inspection apparatus.
Figure 2:
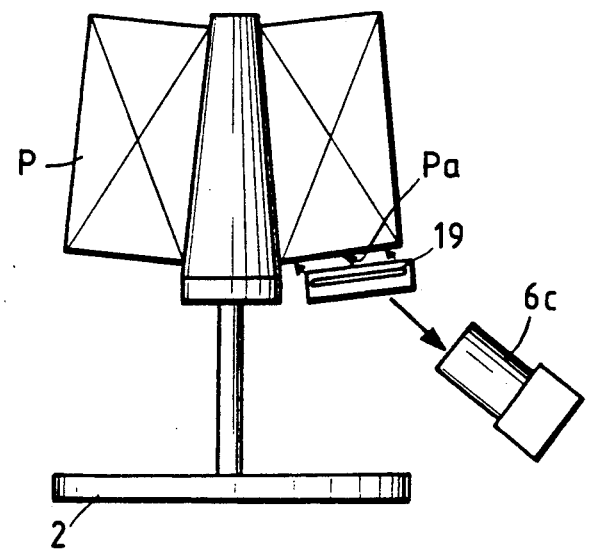
FIG. 2 is a front view showing apparatus for carrying out the method of the present invention.
Figure 3:
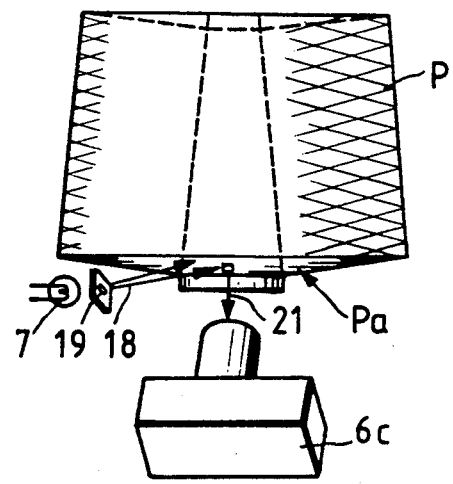
FIG. 3 is a side view thereof.

FIG. 1 shows one example of a surface inspection apparatus for a package.

In FIG. 1, reference numeral 1 denotes a carrier line such as a carrier belt conveyor for transporting a package P wound by a winder (not shown), the package P being mounted on a tray 2 and transported. An inspection box 3 is arranged on the carrier line 1.

The carrier line 1 extends through the inspection box 3 which is formed with an exit 4 through which the package P on the line 1 passes, and a double-leafed hinged door 5 is provided at the exit. This inspection box 3 will be a dark room when the door 5 is closed. There is provided detection means 6 for inspecting various defects of the package P therein by use of various lights such as a visual ray, an ultraviolet ray or the like.

The inspection means 6 includes a camera 6a for detecting a mixture of kinds by applying an ultraviolet ray to the surface of the package P, a camera 6b for detecting a stepped wind by a visual ray, a camera 6c in which light is irradiated from a light source to detect the presence or absence of an out-of-lease from the reflected light, and the like. In addition to those described above, weight detection means for detecting a weight of the package P, and detection means for detecting a stepped wind, wrinkles or a ribbon wind are suitably provided. On the carrier line 1 within the inspection box 3 are provided guide rollers 9, 9 in contact with the outer peripheral portion of the tray 2 to rotate the package P through the tray 2 to detect a defective portion of the whole periphery of the package and a drive roller 10.

On the carrier line on the outlet side of the inspection box 3 is provided a delivery line 11 such as a delivery conveyor perpendicular to the carrier line 1, and delivery means 13 is provided between the carrier line 1 and the delivery line 11, the delivery means 13 comprising a pivotal lever 12 for transferring the defective package P from the carrier line 1 to the delivery line 11.

The delivery means 13 is driven by a defect removal signal 15 from control means 14.

The control means 14 receives various defective signals 16 indicative of defects of the package P detected by the detection means 6 and outputs a defect removal signal 15 to the delivery means 13 delivering the defective package P out of the inspection box 13 to have the package P delivered the delivery line 11.

Next, a method for detecting an out-of-lease on the side of a large diameter package will be described with reference to FIGS. 2 to 5.

There is provided a light source 7 for irradiating a ray 18 in a direction approximately at right angles to an inspection area 17 on a radius line of a surface Pa of a yarn layer of an end on the side of a large diameter of the package P mounted on the tray 2. The light source 7 has a slit 19, and a minimum angle ($\theta$ in FIG. 5) is formed between an approximately parallel ray 18 irradiated from the slit and the surface Pa. The angle ($\theta$) is set as small as possible so that an amount of light which irradiates against an out-of-leased yarn Y reflects, and is provided at an optimum position depending on the structure of the apparatus or the shape of the package.

Figure 4:
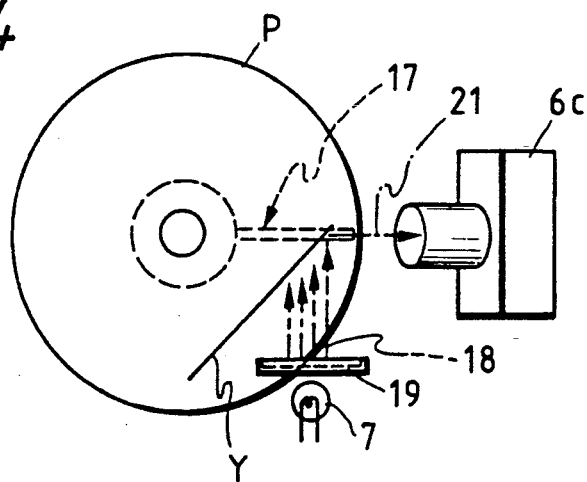
FIG. 4 is a plan view thereof.
Figure 5:
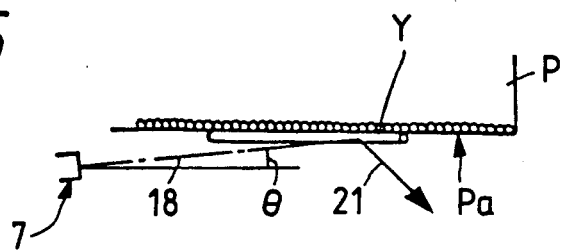
FIG. 5 is an enlarged view showing essential portions.

The camera 6c having a light receiving element such as CCD is provided in the light receiving portion at a position capable of receiving the maximum reflected light of a reflected light 21 obtained by reflecting on an out-of-leased yarn as shown in FIG. 4. As shown in FIG. 4, in case of the above-described embodiment, an incident optical axis of the camera is provided so as to assume a position to be approximately 90° in plane with respect to an optical axis 21 of irradiated light. A straight line Y shown in FIGS. 4 and 5 means a single out-of-lease yarn, and the straight line Y occurs on a tangent line of an arc of a radius about an axis of the package without fail.

Figure 6:
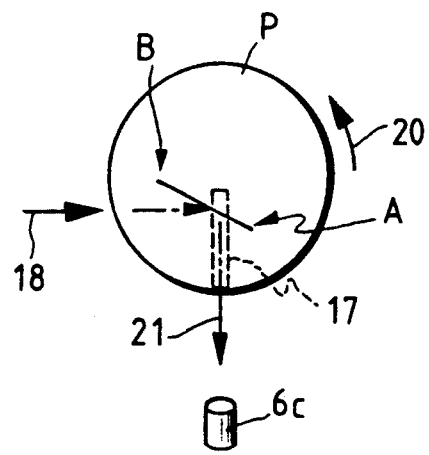
FIGS. 6, 7 and 8 are respectively schematic views showing the relationship between the out-of-lease yarn and the reflected light.
Figure 7:
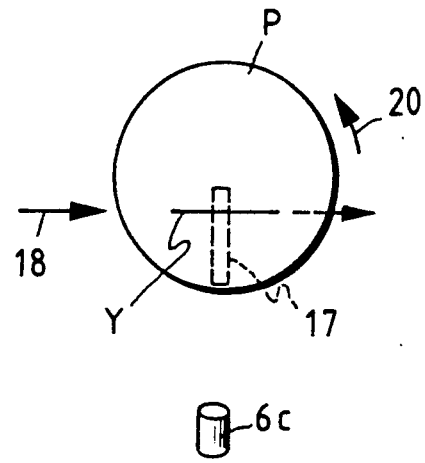
Figure 8:
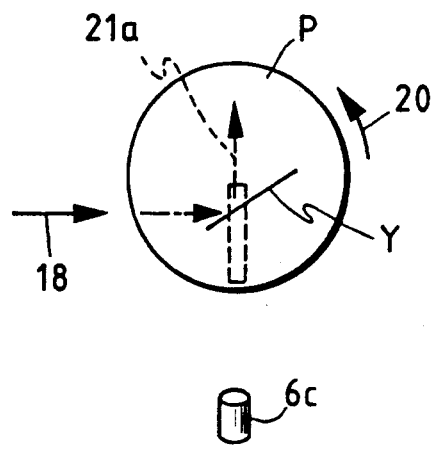

According to the above-described apparatus, as shown in FIGS. 6 to 8, when the package is slowly fully rotated in a direction as indicated by arrow 20 (wherein arrow 18 represents the direction of the irradiated light, 6c the light receiving camera, and frame indicated by broken line 17 the detection area), and one end A and the other end B of the out-of-leased yarn Y is in the state as shown in FIG. 6, the reflected light caused by the out-of-leased yarn Y is great, and a part of optical information level of the detection area obtained by the camera is projected. When the package is further rotated, reflected light caused by the out-of-leased yarn is not produced in the state where the out-of-lease yarn Y is parallel with the optical axis of the irradiated light 18 as shown in FIG. 7 but the irradiated light passes through as it is. At this time, a projection does not occur in a level of light quantities. When the package is further rotated so that the out-of-lease assumes the state of FIG. 8, reflected light 21a of light irradiated on the yarn Y is reflected opposedly of the camera 6c, in which case, also, a projection does not occur in a level of light quantities but conversely, a reversely somewhat projected level is obtained as a thin shadow.

In the above-described apparatus, light information is analyzed by a processing and analyzing device 30 for light information shown in FIG. 9, for example, to detect an out-of-lease.

That is, the light information on the radius line of the package obtained by an image pickup element 31 enters an analyzer 37 via a filter 32, a sample hold circuit 33, an automatic gain control circuit 34 and an amplifier 35, while being converted into a digital signal by an analog/digital converter 36.

The aforesaid digital signal is processed by a difference circuit 38 to obtain signal lines l1 to ln. Each line is one scanning portion. In the case shown, 60 scans were made during one rotation of the package.

In such a graphic representation, a feature portion F can be recognized with the naked eye, and occurrence of an out-of-lease can be substantially judged. However, in case of automating the judgment, further processing of signals is necessary.

Figure 11:
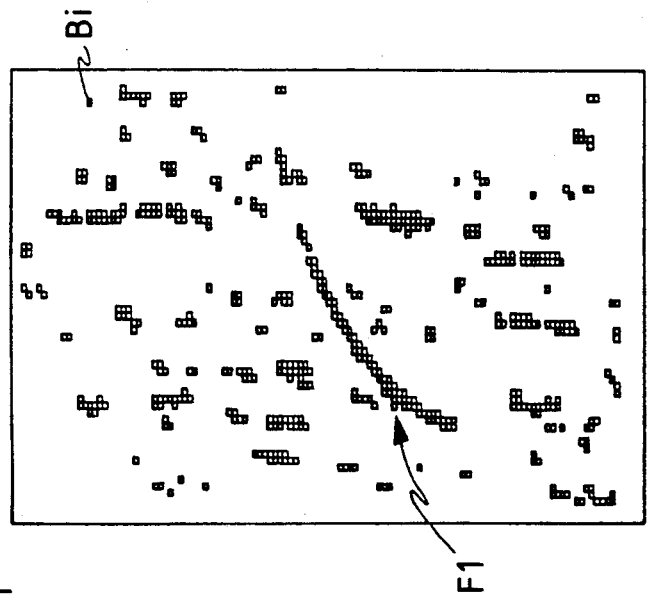
FIG. 11 is a view showing data after binary compression processing.

That is, the signal subjected to difference processing is changed to signal of "0" and "1" by a binary circuit 39, and a fine signal less than a set level is deleted and further compressed in a scanning direction of an image pickup element 31 by a compression circuit 40. The data is thinned out to promote an increase of processing speed. A signal compressed after a signal line of FIG. 10 is formed into a binary is shown in FIG. 11.

That is, signals on the respective scanning lines are indicated at "0" and "1", indicating that a level of reflected light quantities appearing on the scanning line in which one block Bi is present is higher than a set level. Accordingly, it can be visually approximately judged that a continuous portion F1 of a block obliquely indicated in a central portion results from an out-of-lease yarn.

Figure 10:
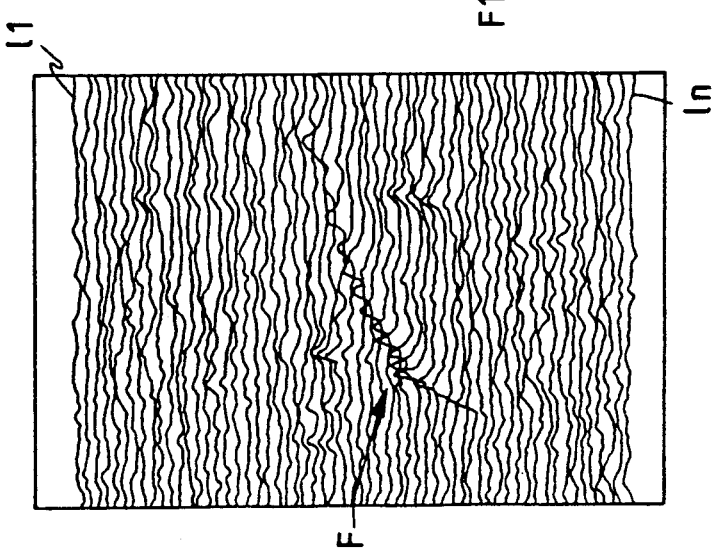
FIG. 10 is a diagram after difference processing by said device.

For automatic judgment, a signal shown in FIG. 10 is inputted into a feature extraction circuit 41 shown in FIG. 9, and it is subjected to processing in accordance with a predetermined system to erase an unnecessary portion. That is, in the case of the present embodiment, when judgment whether or not other block is present in obliquely vertical direction of one unit block is arithmetically operated by an operation formula with respect to all the block, data in which only a feature portion F2 as shown in FIG. 12 is extracted is obtained.

As a result, judgment is made wherein an out-of-lease is present in the package (FIG. 9, 42), and a defect package signal is outputted (43), which is displayed as a print out 44, an image plane display 45 or the like, or a package delivery signal 46 is outputted on the basis of the aforesaid defective package signal. The pivotal lever 12 shown in FIG. 1 is actuated whereby a normal package and a defective package are selected and transported.

Figure 12:
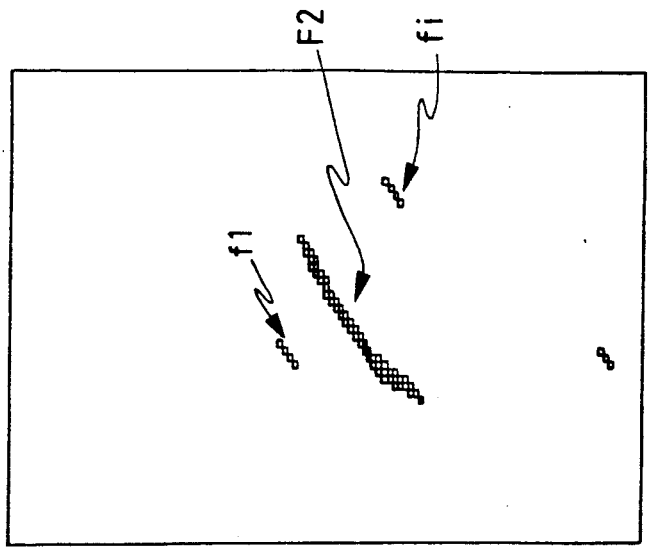
FIG. 12 shows data after extraction of features.

The feature portion F2 representative of the out-of-lease shown in FIG. 12 appears as an image having a length which is half of the actual length of the out-of-lease yarn Y shown in FIGS. 6 to 8. Other portions fl and fi shown in FIG. 12 are not out-of-lease but rugged portions produced on the surface of the yarn layer or adherences such as dirt. Since the number of continuous blocks is less than a predetermined value, they are excluded from a primary factor of judgment of defective packages.

As described above, according to the present invention, it is possible to definitely detect a defective portion appearing on the end of the package, and therefore, it is possible to positively detect a defect such as one wherein a single yarn is out-of-lease.

What is claimed is:

1. A method for detecting an abnormal portion of a package comprising the steps of:

irradiating a ray of light, having an optical axis approximately parallel with a yarn layer surface, against the surface of the package, receiving a reflected beam of light reflected from an abnormal portion of the yarn layer surface, and processing the received beam of light to detect the abnormal portion of the package.

2. A method according to claim 1, wherein the irradiating ray is an approximately parallel ray irradiated from a slit and an angle which is formed between the approximately parallel ray and the yarn layer surface is controlled to be as small as possible.

3. A method according to claim 2, wherein the package is slowly rotated during the irradiating step.

4. A method according to claim 1, wherein the received light beam is converted into a digital signal and the digital signal is processed by a difference circuit to obtain a graphic representation of the abnormal portion of the yarn layer surface.

5. A method according to claim 4, wherein the signal subjected to processing in the difference circuit is converted to a binary signal by a binary circuit to delete a portion of the signal having a value less than a set level, the binary signal being compressed in a scanning direction of an image pick-up element by a compression circuit and provided as an input to a feature extraction circuit to obtain an extracted feature portion.

6. A method according to claim 1, wherein the package comprises a cone-shaped package having a small diameter end face and a large diameter end face, and wherein the step of irradiating a ray of light includes irradiating a ray of light, having an optical axis approximately parallel with a surface portion of the large diameter end face, in a location substantially adjacent to the large diameter end face, thereby enabling detection of an abnormal condition on the large diameter end face of the package.

7. A method for detecting abnormalities in a yarn package having a surface, comprising the steps of:

rotating the yarn package, continuously irradiating a ray of light against the surface of the yarn package, receiving a beam of light reflected from the surface of the yarn package, and processing the received beam of light to detect abnormalities in the yarn package.

8. A method according to claim 7, wherein the step of irradiating comprising irradiating the surface of the package with an approximately parallel ray of light from a slit, and controlling an angle which is formed between the approximately parallel ray and the package surface such that the angle is as small as possible.

9. A method according to claim 7, wherein the step of receiving a reflected beam of light comprises the steps of converting the reflected beam into a digital signal, and processing the digital signal to obtain a graphic representation of a portion of the yarn layer surface.

10. A method according to claim 9, wherein the step of processing the digital signal comprises deleting a portion of the digital signal having a value less than a predetermined level.

11. A method according to claim 7, wherein the yarn package comprises a cone-shaped package having a small diameter end face and a large diameter end face, and wherein the step of irradiating a ray of light comprises irradiating a ray of light having an optical axis approximately parallel with a surface portion of the large diameter end face in a location substantially adjacent to the large diameter end face, thereby enabling detection of an abnormal condition on the large diameter end face of the yarn package.

* * * * *